(12) United States Patent
Gaw

(10) Patent No.: US 9,885,628 B2
(45) Date of Patent: Feb. 6, 2018

(54) RADIOGRAPHIC METHOD AND APPARATUS FOR DETECTION OF CRACKS, DEFECTS, OR LEAK PATHWAYS IN MATERIALS AND ASSEMBLIES

(71) Applicant: The Boeing Company, Chicago, IL (US)

(72) Inventor: Kevin O. Gaw, Seattle, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 15/481,656

(22) Filed: Apr. 7, 2017

(65) Prior Publication Data

US 2017/0254718 A1 Sep. 7, 2017

Related U.S. Application Data

(63) Continuation of application No. 15/062,166, filed on Mar. 6, 2016, now Pat. No. 9,651,447.

(51) Int. Cl.
- *G01M 3/20* (2006.01)
- *G01T 1/18* (2006.01)
- *G01N 15/08* (2006.01)
- *G01N 23/00* (2006.01)

(52) U.S. Cl.
CPC ............ *G01M 3/20* (2013.01); *G01N 15/08* (2013.01); *G01T 1/18* (2013.01); *G01N 23/00* (2013.01); *G01N 2015/0813* (2013.01); *G01N 2015/0846* (2013.01)

(58) Field of Classification Search
CPC .................................. G01M 3/20; G01T 1/18
USPC ................................................. 250/302, 303
See application file for complete search history.

(56) References Cited

U.S. PATENT DOCUMENTS

| 3,621,252 | A | * | 11/1971 | Eddy, Jr. | ............... | G01N 23/043 250/303 |
| 3,997,783 | A | * | 12/1976 | Boutaine | ................. | G01M 3/20 250/303 |
| 5,884,938 | A | * | 3/1999 | Rink | ..................... | B60R 21/264 280/737 |
| 6,530,264 | B1 | * | 3/2003 | Rink | ..................... | G01M 3/227 73/40.7 |
| 6,851,316 | B2 | * | 2/2005 | Micke | ..................... | G01M 3/02 73/40 |

(Continued)

FOREIGN PATENT DOCUMENTS

GB 866977 A1 5/1961

OTHER PUBLICATIONS

International Search Report for United Kingdom Application No. GB1703147.7, date of search Jul. 21, 2017.

*Primary Examiner* — Michael Maskell
(74) *Attorney, Agent, or Firm* — McDonnell Boehnen Hulbert & Berghoff LLP

(57) ABSTRACT

Example systems and methods for testing materials and assemblies for voids, cracks, or other defects are provided. One example system for testing a part includes a chamber configured to accept the part, and a vacuum source connected to the chamber. The example system also includes a fluid source connected to the chamber and configured to provide a radioactive or isotope-labeled fluid to the chamber. In addition, the example system includes a detector configured to detect a presence or absence of radioactivity or the isotope-labeled fluid in the part.

20 Claims, 4 Drawing Sheets

(56) References Cited

U.S. PATENT DOCUMENTS

2014/0102179 A1\* 4/2014 Ekanayake ............... F02C 7/00
  73/40.5 R
2016/0069824 A1\* 3/2016 Bowman ................ G01N 23/18
  378/163
2017/0102285 A1\* 4/2017 Tanaka ................... G01N 23/05

\* cited by examiner ic METHOD AND
APPARATUS FOR DETECTION OF CRACKS,
DEFECTS, OR LEAK PATHWAYS IN
MATERIALS AND ASSEMBLIES

CROSS REFERENCE TO RELATED APPLICATION

The present disclosure is a continuation of U.S. patent application Ser. No. 15/062,166, filed on Mar. 6, 2016, the entire contents of which are herein incorporated by reference.

FIELD

The present disclosure relates generally to radiographic systems and methods for inspecting materials and assemblies, and more particularly, to radiographic systems and methods for detecting voids, cracks, or other defects in materials and assemblies.

BACKGROUND

Proof testing is a nondestructive testing technique for verifying that a part, component, or assembly is suitable to withstand the conditions in which the part, component, or assembly was designed to operate. By way of example, proof testing may involve subjecting a part to twice the part's maximum design load and observing whether the part is damaged in any way. Manufacturers in many industries use proof testing as way to screen a part for manufacturing anomalies before the part is allowed to pass "inspection" and enter service. Similarly, proof testing may also be used to verify that an old part is still functioning properly and is fit for additional service.

In some examples, a part may "pass" proof testing but nevertheless include one or more latent defects. For instance, the proof test might not detect an inconsistency that could cause the part to not be able to sustain a particular design load. Such latent defects may take the form of internal voids, cracks, or other defects that might not be observable from viewing the part's surface. Further, a latent defect might not be detectable using x-ray or ultrasound inspection either. For example, due to the geometry or variable density of the part, x-ray inspection might not be able to detect or reveal a crack in the part. Additionally, x-ray inspection might not be able to detect a crack that is oriented orthogonal to an x-ray detector array. As another example, geometric/material inhomogeneity or latent defects may create additional echoes or shadows, making ultrasound or x-ray data expensive to analyze and making detection of inconsistencies/defects difficult.

SUMMARY

In one example, a method for testing a part is provided. The method includes exposing the part to a radioactive or isotope-labeled fluid under pressure, and, after exposing the part to the radioactive or isotope-labeled fluid under pressure, detecting a presence or absence of radioactivity or the isotope-labeled fluid entrained in the part.

In another example, a system for testing a part is provided. The system comprises a chamber configured to accept the part. The system further comprises a vacuum source connected to the chamber. The system also comprises a fluid source connected to the chamber and configured to provide a radioactive or isotope-labeled fluid to the chamber. Additionally, the system comprises a detector configured to detect a presence or absence of radioactivity or the isotope-labeled fluid in the part.

In still another example, a controller is provided. The controller comprises a processor and a computer-readable medium having stored therein instructions that are executable to cause the controller to perform functions. The functions include causing a vacuum source to reduce a pressure in a chamber, with a part located in the chamber. The functions also include causing a fluid source connected to the chamber to provide a radioactive or isotope-labeled fluid to the chamber. The functions further include causing a fluid reclamation container to remove the radioactive or isotope-labeled fluid from the chamber. And the functions include causing a detector to detect a presence or absence of radioactivity or the isotope-labeled fluid in the part.

The features, functions, and advantages that have been discussed can be achieved independently in various examples or may be combined in yet other examples further details of which can be seen with reference to the following description and figures.

BRIEF DESCRIPTION OF THE FIGURES

The novel features believed characteristic of the illustrative examples are set forth in the appended claims. The illustrative examples, however, as well as a preferred mode of use, further objectives and descriptions thereof, will best be understood by reference to the following detailed description of an illustrative example of the present disclosure when read in conjunction with the accompanying figures, wherein:

DETAILED DESCRIPTION

Figure 1:
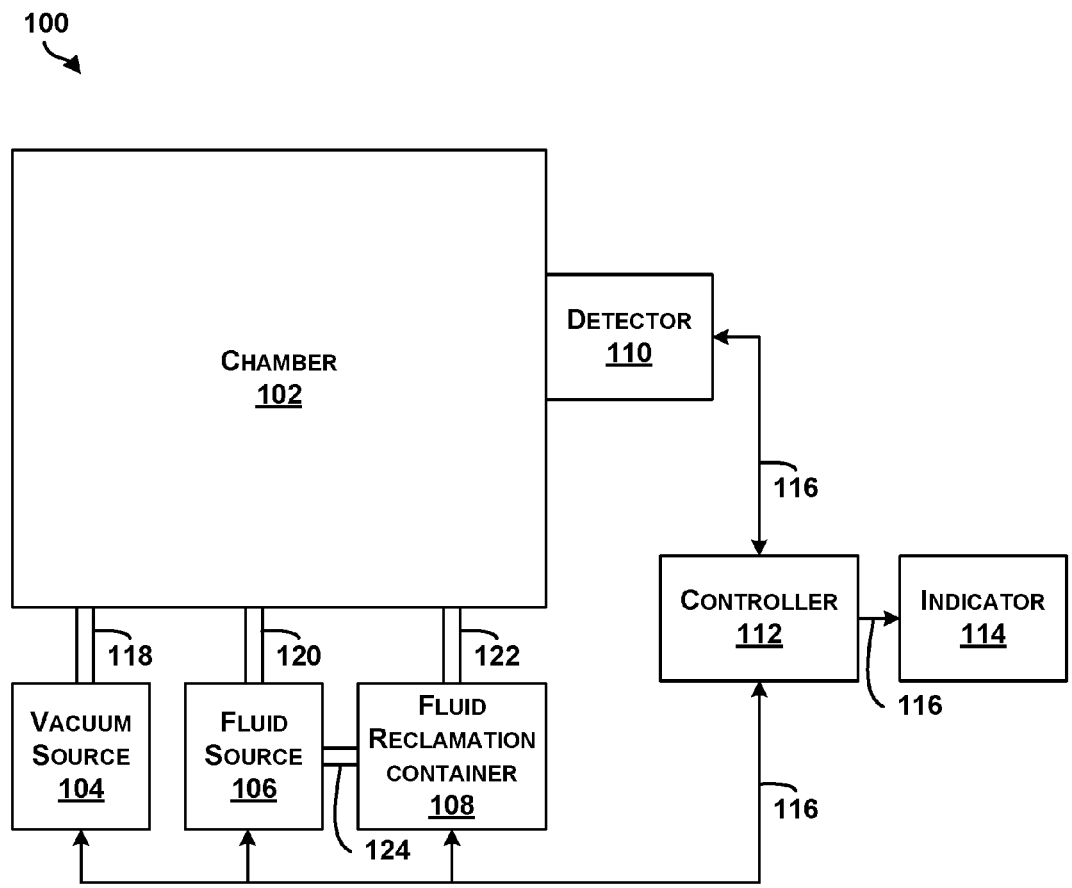
FIG. 1 is a schematic diagram of an example system according to the disclosure.

Disclosed examples will now be described more fully hereinafter with reference to the accompanying figures, in which some, but not all of the disclosed examples are shown. Indeed, several different examples may be provided and should not be construed as limited to the examples set forth herein. Rather, these examples are provided so that this disclosure will be thorough and complete and will fully convey the scope of the disclosure to those skilled in the art.

Within examples, radiographic systems and methods for inspecting materials and assemblies are provided. For instance, the systems and methods may facilitate detecting voids, cracks, or other defects in materials and assemblies. As described herein, the systems and methods leverage the ability of a radioactive or isotope-labeled fluid to permeate through a material or assembly in order to detect the presence or absence of internal defects in the material or assembly. The systems and methods described herein may facilitate detecting defects, such as cracks or voids in parts with complex shape geometries or multiple density/inhomogeneous constituents.

Advantageously, the systems and methods may detect the presence or absence of internal defects without applying loads or pressure (beyond the design loads) on the materials or assemblies. The systems and methods provide an alternative to proof testing. Further, the systems and methods may also facilitate detecting internal cracks or voids that might not otherwise be detectable using other or cost-effective detection techniques. For example, the systems and methods may facilitate detecting latent defects in a part that might not be visible with x-ray inspection due to the orientation of the defect with respect to the detector array or the size and shape of the defect. As another example, the systems and methods may facilitate detecting latent defects in a part that might not be observable with ultrasonic inspection due to the inability of a part to withstand exposure to ultrasound techniques or due to uninterpretable ultrasonic echoes or shadows caused by the geometry or material(s) of the part.

In accordance with examples disclosed herein, an example system includes a chamber, a vacuum source, a fluid source, and a detector. The chamber may be configured to accept a part. For example, the chamber may be an autoclave. The vacuum source may be connected to the chamber and may be configured to remove gas molecules from the chamber and create a partial vacuum in the chamber. The fluid source may also be connected to the chamber and configured to provide a radioactive or isotope-labeled fluid to the chamber. By way of example, after creating a partial vacuum in the chamber and while the part is in the chamber, the fluid source may provide the radioactive or isotope-labeled fluid to the chamber.

Within the chamber, the radioactive or isotope-labeled fluid may then permeate through the part. For instance, the part may have a permeable surface or the part may be a polymeric composite or polymeric part, thereby being permeable to the radioactive or isotope-labeled fluid, which can permeate through the part. If the part includes any internal cracks or voids, the radioactive or isotope-labeled fluid may then permeate into the cracks or voids and become entrained or trapped within the defects. The presence of the entrained fluid may then detectable by an x-ray detector, for instance.

The detector may then be used to detect a presence or absence of radioactivity or the isotope-labeled fluid in the part. By way of example, if the part was exposed to a radioactive fluid, the detector may be configured to detect the presence or absence of radioactivity entrained in the part. On the other hand, if the part was exposed to an isotope-labeled fluid, the detector may be configured to detect the presence or absence of the isotope-labeled fluid entrained in the part. In one example, the detector may be connected to the chamber and configured to detect the presence or absence of radioactivity or the isotope-labeled fluid after removal of the radioactive or isotope-labeled fluid from the chamber. Alternatively, the detector may be separate from the chamber and the part may be removed from the chamber to a location of the detector. In one example, the detector may be an x-ray detector.

If the detector detects the presence of radioactivity or the isotope-labeled fluid (e.g., more than a threshold detectable amount of radioactivity or more than a threshold amount of isotope-labeled fluid), the presence of the radioactivity or the isotope-labeled fluid may be interpreted to mean that the part potentially contains a latent defect. For example, the detector may detect radioactivity or isotope-labeled fluid entrained within the part or emanating from a void or crack within the part. On the other hand, if the detector detects an absence of radioactivity or absence of the isotope-labeled fluid (e.g., less than a threshold concentration), the absence of the radioactivity or isotope-labeled fluid may be interpreted to mean that the part does not include any significant latent defects.

Various other features of the example system discussed above, as well as methods for testing a part using these systems, are also described hereinafter with reference to the accompanying figures.

Referring to the figures, FIG. 1 is a schematic diagram of an example system 100. In line with the discussion above, the example system 100 may be used to test a part. As shown in FIG. 1, the example system 100 includes a chamber 102, a vacuum source 104, a fluid source 106, a fluid reclamation container 108, a detector 110, a controller 112, and an indicator 114.

As shown in FIG. 1, the controller 112 may be coupled to the vacuum source 104, fluid source 106, fluid reclamation container 108, detector 110, and indicator 114 via one or more wired or wireless links, system buses, networks, or other connection mechanisms 116. In addition, each of the vacuum source 104, fluid source 106, and fluid reclamation container 108 may be coupled to the chamber via fluid pathways 118, 120, 122. Further, the fluid source 106 may be coupled to the fluid reclamation container 108 via a fluid pathway 124.

The chamber 102 may be configured to accept a part. In one example, the chamber 102 may be an autoclave. More generally, the chamber 102 may be any cavity or space that may enclose a part and be sealed for a period of time. For example, the chamber 102 may have a pressure-tight lid or door that may be opened to insert a part and closed to facilitate exposing the part to a radioactive or isotope-labeled fluid under pressure.

The vacuum source 104 may be connected to the chamber 102 and configured to regulate the pressure in the chamber 102. In particular, the vacuum source 104 may be configured to create a partial vacuum in the chamber 102 by removing gas molecules from the chamber 102. By way of example, the vacuum source 104 may be a vacuum pump. In an example in which the chamber 102 is an autoclave, the vacuum source 104 may be an integrated component of the autoclave.

The fluid source 106 may be configured to provide a radioactive or isotope-labeled fluid to the chamber 102. In one example, the fluid source 106 may store the radioactive or isotope-labeled fluid and include a valve for releasing the radioactive or isotope-labeled fluid into the chamber 102 via the fluid pathway 120. The radioactive or isotope-labeled fluid may take any of a variety of forms, depending on the desired configuration. The fluid source 106 may provide a radioactive gas, such as radon, radioactive helium, or radioactive xenon. Alternatively, the fluid source 106 may provide a radioactive liquid. The isotope-labeled fluid may be radioactive or non-radioactive. Further the isotope-labeled fluid may be a liquid (e.g., deuterated water) or a gas (e.g., deuterated methane or helium-3).

Once the fluid source 106 provides the radioactive or isotope-labeled fluid to the chamber 102, the radioactive or isotope-labeled fluid may permeate into the part. The amount of time that the part is exposed to the radioactive or isotope-labeled fluid in the chamber may vary, depending on the desired configuration. In practice, the permeation of the radioactive or isotope-labeled fluid is related to the concentration gradient of the radioactive or isotope-labeled gas, the location of the defect, and the part's intrinsic permeability. The permeation of the fluid through the part could be modeled using Fick's laws of diffusion, and exposure times may be calculated accordingly. Deviations from obedience to Fick's law may be an indication of the location of defects in the part.

The fluid reclamation container 108 may be configured to remove the radioactive or isotope-labeled fluid from the chamber after the permeation. By way of example, the fluid reclamation container 108 may include a vacuum pump and cooler configured to reclaim the radioactive or isotope-labeled fluid from the chamber 102 and a storage container configured to store the radioactive or isotope-labeled fluid. The fluid reclamation container 108 may take other forms as well.

In some instances, the radioactive or isotope-labeled fluid may be recycled for use in subsequent testing. For example, the fluid reclamation container 108 may collect the radioactive or isotope-labeled fluid, and during a subsequent test, the fluid source 106 may provide the collected radioactive or isotope-labeled to the chamber 102 via the pathways 120 and 124. In other instances, the radioactive or isotope-labeled fluid reclaimed by the reclamation container 108 may be discarded and might not be reused.

The detector 110 may be configured to detect a presence or absence of radioactivity or isotope-labeled fluid in the part. By way of example, if the part was exposed to a radioactive fluid, the detector may be configured to detect a presence or absence of radioactivity entrained in the part. On the other hand, if the part was exposed to an isotope-labeled fluid, the detector may be configured to detect a presence or absence of the isotope-labeled fluid entrained in the part. The detector may be an x-ray detector (e.g., a digital x-ray detector or a Geiger counter).

The detector may be connected to the chamber and configured to detect the presence or absence of radioactivity or the isotope-labeled fluid entrained in the part after removal of the radioactive or isotope-labeled fluid from the chamber. The detector may be separate from the chamber (not shown) and configured to detect the presence or absence of the radioactivity or isotope-labeled fluid entrained in the part after removal of the part from the chamber The controller 112 may be configured to control one or more of the vacuum source 104, fluid source 106, fluid reclamation container 108, detector 110, and indicator 114 in order to carry out testing of a part in accordance with the methods described herein. By way of example, the controller 112 may be configured to send instructions to the vacuum source 104 causing the vacuum source to create a partial vacuum in the chamber 102. The controller may also be configured to send instructions to the fluid source 106 causing the fluid source 106 to provide a radioactive or isotope-labeled fluid to the chamber 102. Additionally, the controller may be configured to send instructions to the fluid reclamation container 108 causing the fluid reclamation container 108 to reclaim the radioactive or isotope-labeled fluid from the chamber 102. The controller 112 may also be configured to send instructions to the detector 110 causing the detector to detect a presence or absence of radioactivity or isotope-labeled fluid entrained in the part.

One or more of the vacuum source 104, fluid source 106, fluid reclamation container 108, and detector 110 may be controlled manually (e.g., by an operator) without being controlled by the controller 112. Alternatively, the controller 112 and the indicator 114 may be omitted from the system 100 altogether (not shown).

In some examples, the controller 112 may be configured to receive data from the detector 110 indicating a presence or absence of radioactivity or isotope-labeled fluid, and send instructions to the indicator 114 causing the indicator 114 to provide an indication of the presence or absence of the radioactivity or isotope-labeled fluid in the part.

The indicator 114 may function to provide an output that is indicative of the presence or absence of radioactivity or isotope-labeled fluid in a part. As such, the indicator 114 may comprise a light source (e.g., a light emitting diode) that is configured to provide a green or red light, depending on whether the radioactivity or isotope-labeled fluid is present. Alternatively, the indicator 114 may comprise an electroacoustic transducer (e.g., a speaker) that is configured to provide an audible noise or alarm when radioactivity or isotope-labeled fluid is present. The indicator 114 may take other forms as well. The indicator 114 may be an integrated component of the controller 112.

Figure 2:
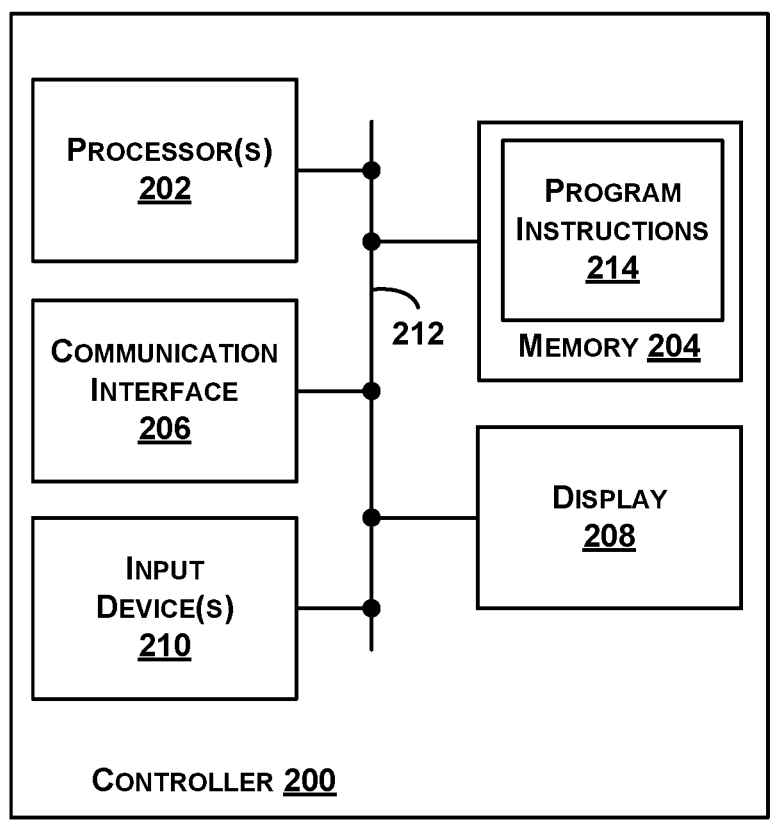
FIG. 2 is a schematic diagram of an example controller according to the disclosure.

FIG. 2 is a schematic diagram of an example controller 200. The controller 200 in FIG. 2 may represent the controller 112 (see FIG. 1). The controller 200 may be or include a computer, mobile device, or similar device that may be configured to perform the functions described herein.

As shown in FIG. 2, the controller 200 may include one or more processors 202, a memory 204, a communication interface 206, a display 208, and one or more input devices 210. Components illustrated in FIG. 2 may be linked together by a system bus, network, or other connection mechanism 212. The controller 200 may also include hardware to enable communication within the controller 200 and between the controller 200 and one or more other devices, such as any of the components of the system 100 (see FIG. 1). The hardware may include transmitters, receivers, and antennas, for example.

The one or more processors 202 may be any type of processor, such as a microprocessor, digital signal processor, multicore processor, etc., coupled to the memory 204. The memory 204 may be any type of memory, such as volatile memory like random access memory (RAM), dynamic random access memory (DRAM), static random access memory (SRAM), or non-volatile memory like read-only memory (ROM), flash memory, magnetic or optical disks, or compact-disc read-only memory (CD-ROM), among other devices used to store data or programs on a temporary or permanent basis.

Additionally, the memory 204 may be configured to store program instructions 214. The program instructions 214 may be executable by the one or more processors 202. For instance, the program instructions 214 may be executable to cause a vacuum source to reduce a pressure in a chamber, cause a fluid source connected to the chamber to provide a radioactive or isotope-labeled fluid to the chamber, cause a fluid reclamation container to remove the radioactive or isotope-labeled fluid from the chamber, and/or cause a detector to detect a presence or absence of radioactivity or isotope-labeled fluid in a part. The program instructions 214 may also be executable to cause the one or more processors 202 to perform other functions, such as any of the functions described herein.

The communication interface 206 may be configured to facilitate communication with one or more other devices, in accordance with one or more wired or wireless communication protocols. For example, the communication interface 206 may be configured to facilitate wireless data communication for the controller 200 according to one or more wireless communication standards, such as one or more IEEE 802.11 standards, ZigBee standards, Bluetooth standards, etc. As another example, the communication interface 206 may be configured to facilitate wired data communication with one or more other devices.

The display 208 may be any type of display component configured to display data. As one example, the display 208 may include a touchscreen display. As another example, the display may include a flat-panel display, such as a liquid-crystal display (LCD) or a light-emitting diode (LED) display.

The one or more input devices 210 may include one or more pieces of hardware equipment used to provide data and control signals to the controller 200. For instance, the one or more input devices 210 may include a mouse or pointing device, a keyboard or keypad, a microphone, a touchpad, or a touchscreen, among other possible types of input devices.

Figure 3:
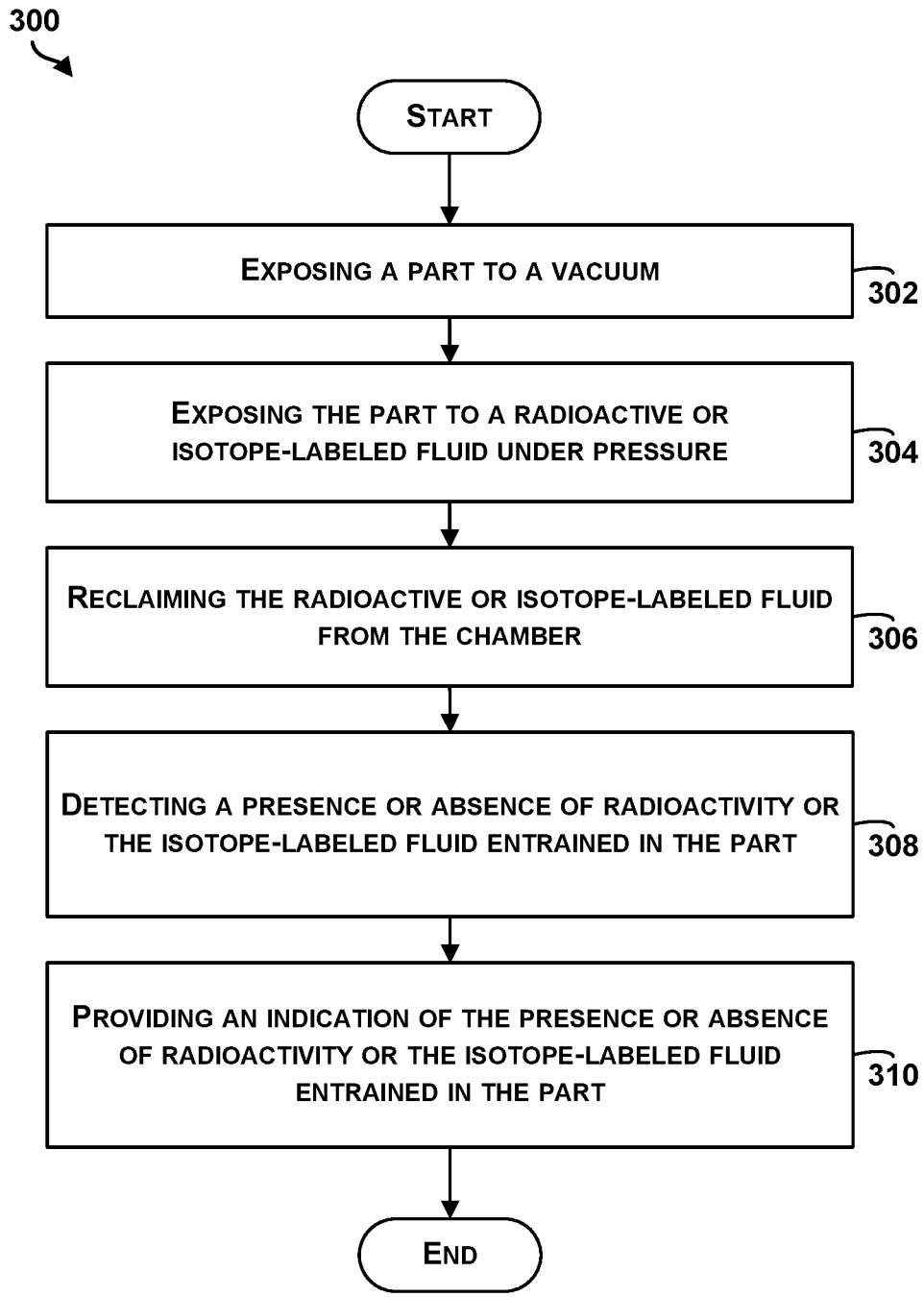
FIG. 3 is a flowchart of an example method for testing a part according to the disclosure.

FIG. 3 is a flowchart of an example method for testing a part. Method 300 shown in FIG. 3 presents a method that, for example, could be used with the system 100 (see FIG. 1), or any of the systems disclosed herein. Example devices or systems may be used or configured to perform logical functions presented in FIG. 3. In some instances, components of the devices and/or systems may be configured to perform the functions such that the components are actually configured and structured (with hardware and/or software) to enable such performance. In other examples, components of the devices and/or systems may be arranged to be adapted to, capable of, or suited for performing the functions. Method 300 may include one or more operations, functions, or actions as illustrated by one or more of blocks 302-310. Although these blocks are illustrated in a sequential order, these blocks may also be performed in parallel, and/or in a different order than those described herein. Also, the various blocks may be combined into fewer blocks, divided into additional blocks, and/or removed based upon the desired implementation.

It should be understood that for this and other processes and methods disclosed herein, flowcharts show functionality and operation of one possible implementation of present disclosure. In this regard, each block may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. The computer readable medium may include non-transitory computer readable medium or memory, for example, such as computer readable media that stores data for short periods of time like register memory, processor cache, and RAM. The computer readable media may also be any other volatile or non-volatile storage systems. The computer readable medium may be considered a tangible computer readable storage medium, for example.

In addition, each block in FIG. 3 may represent circuitry that is wired to perform the specific logical functions in the process. Alternative implementations are included within the scope of the examples of the present disclosure in which functions may be executed out of order from that shown or discussed, including substantially concurrent or in reverse order, depending on the functionality involved.

Initially, at block 302, the method 300 includes exposing a part to a vacuum. In line with the discussion above, the part may be placed in a chamber, and a vacuum source may create a partial vacuum in the chamber. The part may be exposed to a vacuum in an autoclave.

At block 304, the method 300 includes exposing the part to a radioactive or isotope-labeled fluid under pressure. As discussed above, a fluid source may provide the radioactive or isotope-labeled fluid to a chamber in which the part is located. The radioactive or isotope-labeled fluid may be a gas or a liquid. Within the chamber, the radioactive or isotope-labeled fluid may then permeate into any cracks or voids within the part. The pressure within the voids or cracks may be less than the pressure within the chamber. Thus, the radioactive or isotope-labeled fluid may tend to permeate be retained in the voids or cracks.

At block 306, the method 300 includes reclaiming the radioactive or isotope-labeled fluid from the chamber. In line with the discussion above, the radioactive or isotope-labeled fluid may be removed from the chamber and collected. Optionally, the radioactive or isotope-labeled fluid may be recycled and used again during subsequent testing.

At block 308, the method 300 includes detecting a presence or absence of radioactivity or the isotope-labeled fluid entrained in the part. By way of example, if the part was exposed to a radioactive fluid at block 304, then the detector may be configured to detect a presence or absence of radioactivity entrained in the part. On the other hand, if the part was exposed to an isotope-labeled fluid at block 304, then the detector may be configured to detect a presence or absence of the isotope-labeled fluid entrained in the part. The detector may detect a concentration of radioactivity or isotope-labeled fluid. For instance, a Geiger counter may determine the concentration. The detector or a separate controller may then determine whether the concentration satisfies a predetermined criterion. For instance, the detector or controller may compare the detected concentration to a threshold concentration.

In another example, a digital x-ray detector may generate an image of the part. If there is any radioactivity or isotope-labeled fluid entrained in the part, the radioactivity or isotope-labeled fluid may be observable in the image. The digital x-ray detector may generate the image without using an x-ray source. The digital x-ray detector or a separate controller may then analyze the image to determine whether the image is indicative of the presence of radioactive or isotope-labeled fluid in the part. Alternatively, a technician may review the image to determine whether the image is indicative of the presence of radioactivity or isotope-labeled fluid in the part.

At block 310, the method 300 includes providing an indication of the presence or absence of the radioactivity or the isotope-labeled fluid entrained in the part. For example, if the detector is configured to detect a presence or absence of radioactivity, an indicator may provide a green indication indicating the absence of radioactivity and that the part does not appear to include any latent defects. Alternatively, the indicator may provide a red indication indicating the presence of radioactivity and that the part appears to have a sub-surface latent defect. Similarly, if the detector is configured to detect a presence or absence of isotope-labeled fluid, an indicator may provide a green indication indicating the absence of isotope-labeled fluid (e.g., less than a threshold detectable concentration), or provide an indication indicating the presence of the isotope-labeled fluid.

In response to detecting the presence of radioactivity or isotope-labeled fluid, the method 300 may further include testing the part using a secondary inspection technique. Examples of secondary inspection techniques include x-ray detection, magnetic resonance imaging (MRI), and computerized axial tomography (CAT) scanning, among others. The secondary inspection technique may be used to visualize any latent defects within the part.

Figure 4:
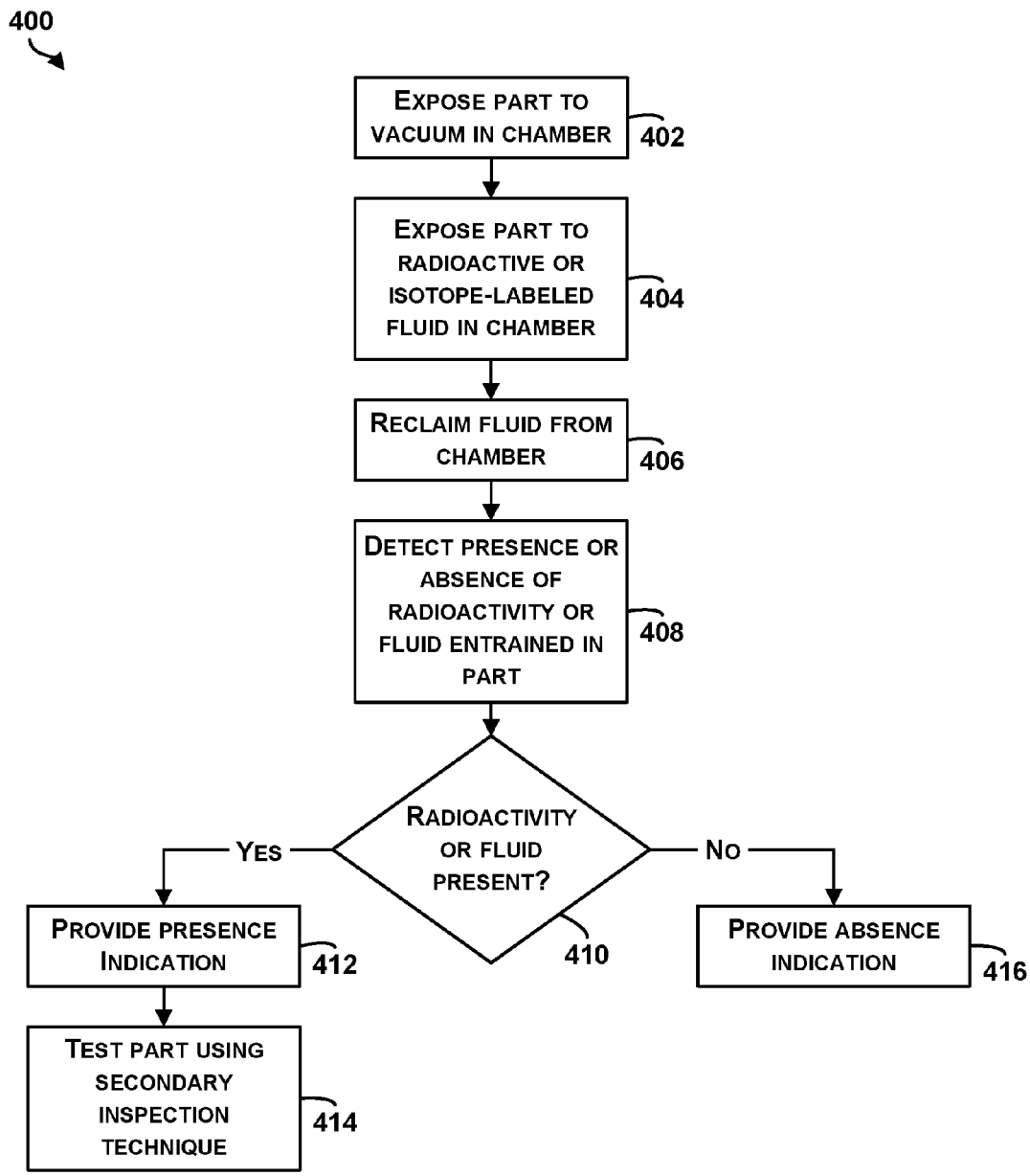
FIG. 4 is a flowchart of another example method for testing a part according to the disclosure.

FIG. 4 is a flowchart of another example method for evaluating a surface of an object. Method 400 may include one or more operations, functions, or actions as illustrated by blocks 402-416 of the flowchart. Although the blocks are illustrated in a sequential order, these blocks may also be performed in parallel, and/or in a different order than those described herein. Also, the various blocks may be combined into fewer blocks, divided into additional blocks, and/or removed from the flowchart, based upon the desired implementation of the method 400. Each block may represent a module, segment, or a portion of program code, which includes one or more instructions executable by a processor for implementing specific logical functions or steps in the process. In addition, each block in FIG. 4 may represent circuitry that is wired to perform the specific logical functions in the process.

Initially, at block 402, the method 400 involves exposing a part to a vacuum in a chamber. At block 404, the method 400 involves exposing the part to a radioactive or isotope-labeled fluid in the chamber. At block 406, the method 400 involves reclaiming the radioactive or isotope-labeled fluid from the chamber.

Further, at block 408, the method 400 involves detecting a presence or absence of radioactivity or the isotope-labeled fluid entrained in the part. If radioactivity or isotope-labeled fluid is present, then at block 412, the method 400 involves providing a presence indication, and, at block 414, the method 400 involves testing the part using a secondary inspection technique. Whereas, if radioactivity or isotope-labeled fluid is absent, then, at block 416, the method 400 involves providing an absence indication, and an operator may then proceed to testing another part.

The description of the different advantageous arrangements has been presented for purposes of illustration and description, and is not intended to be exhaustive or limited to the examples in the form disclosed. After reviewing and understanding the foregoing disclosure, many modifications and variations will be apparent to those of ordinary skill in the art. Further, different examples may provide different advantages as compared to other examples. The example or examples selected are chosen and described in order to best explain the principles, the practical application, and to enable others of ordinary skill in the art to understand the disclosure for various examples with various modifications as are suited to the particular use contemplated.

What is claimed is:

1. A method for testing a part, comprising:
exposing, in a chamber, a part having a permeable surface to a radioactive or isotope-labeled fluid under pressure to enable the radioactive or isotope-labeled fluid to permeate into a sub-surface crack or a sub-surface void defect internal to the part and become entrained within the sub-surface crack or the sub-surface void defect internal to the part; and
after exposing the part to the radioactive or isotope-labeled fluid under pressure, detecting a presence or absence of radioactivity or the isotope-labeled fluid entrained within the sub-surface crack or the sub-surface void defect internal to the part to detect a presence or absence of a sub-surface latent defect of the part.

2. The method of claim 1, wherein the part is a polymeric composite part comprising multiple materials, and exposing the part to the radioactive or isotope-labeled fluid under pressure comprises:
enabling the radioactive or isotope-labeled fluid to permeate into the sub-surface crack or the sub-surface void defect between the multiple materials.

3. The method of claim 1, wherein the part comprises materials having multiple density or inhomogeneous constituents, and exposing the part to the radioactive or isotope-labeled fluid under pressure comprises:
enabling the radioactive or isotope-labeled fluid to permeate into the sub-surface crack or the sub-surface void defect of the multiple density or inhomogeneous constituents.

4. The method of claim 1, further comprising:
exposing the part to the radioactive or isotope-labeled fluid under pressure by providing the radioactive or isotope-labeled fluid from a fluid source to the chamber.

5. The method of claim 4, further comprising:
reclaiming the radioactive or isotope-labeled fluid from the chamber and providing the radioactive or isotope-labeled fluid back to the fluid source via a pathway.

6. The method of claim 1, further comprising:
exposing the part to a vacuum before exposing the part to the radioactive or isotope-labeled fluid under pressure.

7. The method of claim 1, further comprising detecting the presence or absence of radioactivity or the isotope-labeled fluid entrained within the sub-surface crack or the sub-surface void defect of the part using an x-ray detector.

8. The method of claim 1, further comprising providing an indication of the presence or absence of radioactivity or the isotope-labeled fluid entrained within the sub-surface crack or the sub-surface void defect of the part.

9. The method of claim 1, further comprising:
based on detecting the presence of the radioactive or isotope labeled fluid entrained within the sub-surface crack or the sub-surface void defect of the part, inspecting the part using a secondary inspection technique.

10. The method of claim 9, wherein the secondary inspection technique includes one or more of magnetic resonance imaging (MRI) and computerized axial tomography (CAT) scanning to visualize the sub-surface crack or the sub-surface void defect of the part.

11. The method of claim 1, further comprising:
determining a location of the sub-surface crack or the sub-surface void defect of the part.

12. A system for testing a part, comprising:
a vacuum source connected to a chamber configured to accept a part having a permeable surface;
a fluid source connected to the chamber and configured to provide a radioactive or isotope-labeled fluid to the chamber to expose the part to the radioactive or isotope-labeled fluid under pressure and enable the radioactive or isotope-labeled fluid to permeate into a sub-surface crack or a sub-surface void defect internal to the part and become entrained within the sub-surface crack or the sub-surface void defect internal to the part; and
a detector configured to detect a presence or absence of radioactivity or the isotope-labeled fluid entrained within the sub-surface crack or the sub-surface void defect internal to the part to detect a presence or absence of a sub-surface latent defect of the part.

13. The system of claim 12, further comprising:
a fluid reclamation container connected to the chamber and to the fluid source, the fluid reclamation container configured to remove the radioactive or isotope-labeled fluid from the chamber and provide the removed radioactive or isotope-labeled fluid back to the fluid source via a pathway.

14. The system of claim 12, wherein the detector is connected to the chamber and configured to detect the presence or absence of radioactivity or the isotope-labeled fluid entrained within the sub-surface crack or the sub-surface void defect of the part after removal of the radioactive or isotope-labeled fluid from the chamber.

15. The system of claim 12, wherein the detector is connected to the chamber.

16. The system of claim 12, wherein the detector comprises an x-ray detector.

17. The system of claim 16, wherein the x-ray detector comprises a Geiger counter.

18. The system of claim 12, further comprising:
an indicator configured to provide an indication of the presence or absence of radioactivity or the isotope-labeled fluid entrained within the sub-surface crack or the sub-surface void defect of the part.

19. A controller comprising:
a processor; and
a computer-readable medium having stored therein instructions that are executable to cause the controller to perform functions comprising:
  causing a vacuum source to reduce a pressure in a chamber, wherein a part having a permeable surface is located in the chamber,
  causing a fluid source connected to the chamber to provide a radioactive or isotope-labeled fluid to the chamber to enable the radioactive or isotope-labeled fluid to permeate into a sub-surface crack or a sub-surface void defect internal to the part and become entrained within the sub-surface crack or the sub-surface void defect internal to the part, and
  causing a detector to detect a presence or absence of radioactivity or isotope-labeled fluid entrained within the sub-surface crack or the sub-surface void defect internal to the part to detect a presence or absence of a sub-surface latent defect of the part.

20. The controller of claim 19, wherein the functions further comprising:
causing an indicator to provide an indication of the presence or absence of radioactivity or isotope-labeled fluid entrained within the sub-surface crack or the sub-surface void defect of the part.

* * * * *